United States Patent [19]

Stokes

[11] 4,262,678
[45] Apr. 21, 1981

[54] PACING LEAD WITH TINE PROTECTOR

[75] Inventor: Kenneth B. Stokes, Brooklyn Park, Minn.

[73] Assignee: Medtronic, Inc., Minneapolis, Minn.

[21] Appl. No.: 53,002

[22] Filed: Jun. 28, 1979

[51] Int. Cl.³ ............................................. A61N 1/04
[52] U.S. Cl. .................................................. 128/786
[58] Field of Search .................... 128/419 P, 784–786; 206/315 R, 363, 364, 365, 367, 438; 273/415, 419, 425; 211/60 R, 60 A, 65

[56] References Cited

U.S. PATENT DOCUMENTS

| | | | |
|---|---|---|---|
| 2,460,230 | 1/1949 | Makrianes | 211/60 A |
| 3,960,271 | 6/1976 | Nelson | 206/315 R |
| 4,181,220 | 1/1980 | Zicko | 211/60 A |

FOREIGN PATENT DOCUMENTS

| | | | |
|---|---|---|---|
| 2252088 | 5/1973 | Fed. Rep. of Germany | 211/60 R |
| 1047589 | 7/1953 | France | 211/60 A |

*Primary Examiner*—William E. Kamm
*Attorney, Agent, or Firm*—John L. Rooney; Lew Schwartz; Joseph F. Breimayer

[57] ABSTRACT

Tine protector which protects a plurality of outwardly angular extending tines from an electrode of a pacing lead. The tine protector includes four sides and a bottom where two of the opposing sides include a first round hole in one side, and a second round hole joined to a longitudinal vertical slit in the other side. The electrode frictionally engages into the first hole, and the other electrode or lead of the pacing lead frictionally engages down through the slit and into the second hole. The tines are protected by their close proximity to these two opposing sides.

4 Claims, 4 Drawing Figures

PACING LEAD WITH TINE PROTECTOR

BACKGROUND OF THE INVENTION

1. Field of the Invention

The present invention relates generally to a package, and more particularly, pertains to a package for protecting tines of a pacing lead for a pulse generator.

2. Description of the Prior Art

It has been a prior art practice to package pacing leads in plastic packages which are suitable for sterilizing such as with gas or autoclaving. The pacing lead in the past has been inserted into the package and has laid flat within the package during transportation, storage, and sterilizing prior to use in an individual. While this has been satisfactory for the prior art pacing leads, with the advent of new tined pacing leads, the tines have displayed amounts of nonconformity after being transported, stored, and sterilized. Such deformation is less than satisfactory from a medical point of view.

Pacing leads with tines have exhibited a certain amount of creep and deformation of the tines resulting in a change of the physical characteristics of the pacing lead.

One prior art practice has now been to insert a ring-tip electrode having outwardly angular extending tines into the hole of a rectangular rubber member. This type of tine protector somewhat accomplished the end result of preventing creep and deformation of the tines but was less than one hundred percent satisfactory.

The present invention overcomes the disadvantages of the prior art problems by providing a tine protector for protecting the tines spaced about an electrode of a pacing lead.

SUMMARY OF THE INVENTION

The present invention provides protection for tines, spaced about an electrode of a pacing lead, from deformation, creep and other stress during sterilization, transportation and storage of the pacing lead. Also protected is the fixation loop of a transvenous electrode with a fixation loop from creep and deformation during sterilization, transportation and storage.

According to one embodiment of the present invention, there is provided a tine protector for protecting an electrode having a plurality of angularly spaced tines of a pacing lead including four sides and a bottom connecting the four sides together, a first round hole located in one of the sides and a vertical longitudinal slit and second round hole geometrically located in the opposing side whereby the first hole accommodates the electrode and the second hole accommodates the lead of the pacing lead thereby enclosing the tines spaced about the electrode within the five-sided enclosure.

A significant aspect and feature of the present invention is a package having a structure which is suitable for use in an autoclave which permits positioning a pacing lead in the tine protector and subsequent packaging in a package which is then sterilized in an autoclave or by gas.

The tine protector of the present invention can be at least a four-sided object or a five-sided object where the fifth side provides physical structural support for the four sides.

The tine protector of the present invention can be manufactured of non-woven polypropolene material, silicone rubber and paper. These materials also include the plastic family.

The tine protector of the present invention prevents creep and deformation of the tines and provides physical support to the electrode about the junction of the electrode and the pacing lead.

BRIEF DESCRIPTION OF THE DRAWINGS

Other objects and many of the attendant advantages of this invention will be readily appreciated as the same becomes better understood by reference to the following detailed description when considered in connection with the accompanying drawing, in which like reference numerals designate like parts throughout the FIGURES thereof and wherein.

DESCRIPTION OF THE PREFERRED EMBODIMENT

Figure 1:
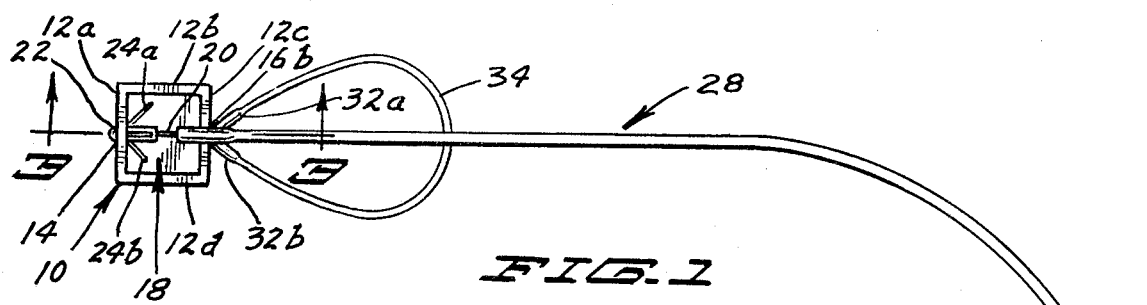
FIG. 1 is a plan view of a tine protector supporting transvenous leads with a fixation loop.
Figure 2:
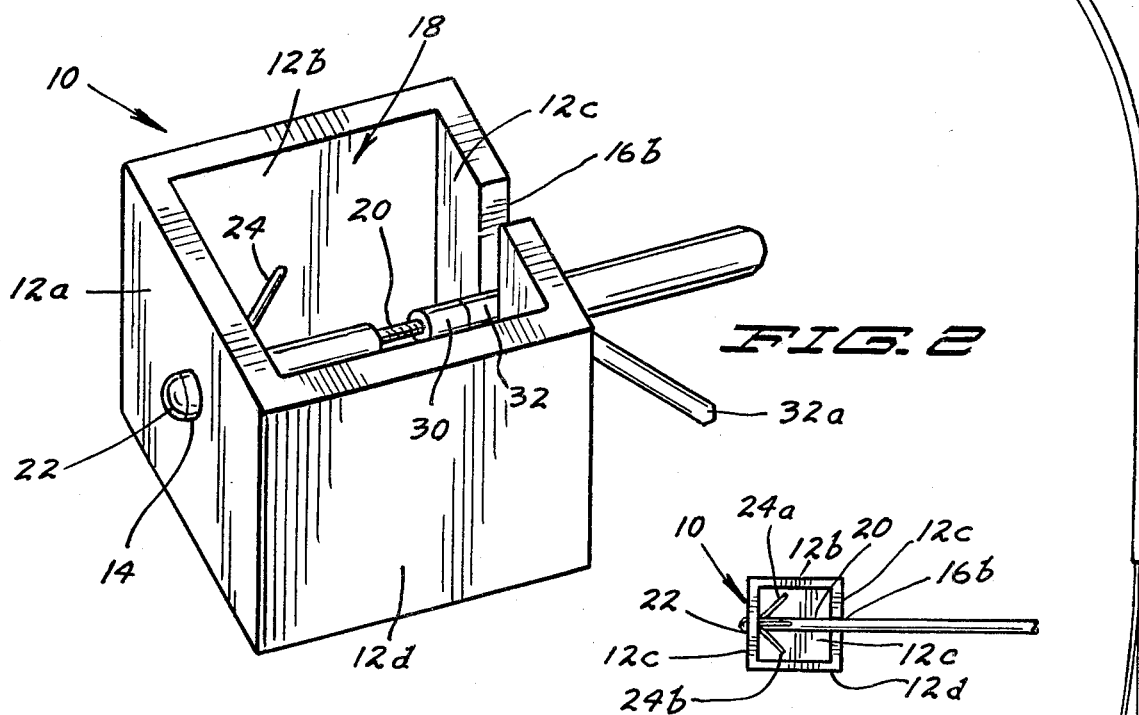
FIG. 2 is a perspective view of the tine protector with the transvenous leads in position including the electrode extending through a first hole in the tine protector and a ring electrode extending down through a longitudinal vertical slit and resting in a second hole of the tine protector.
Figure 3:
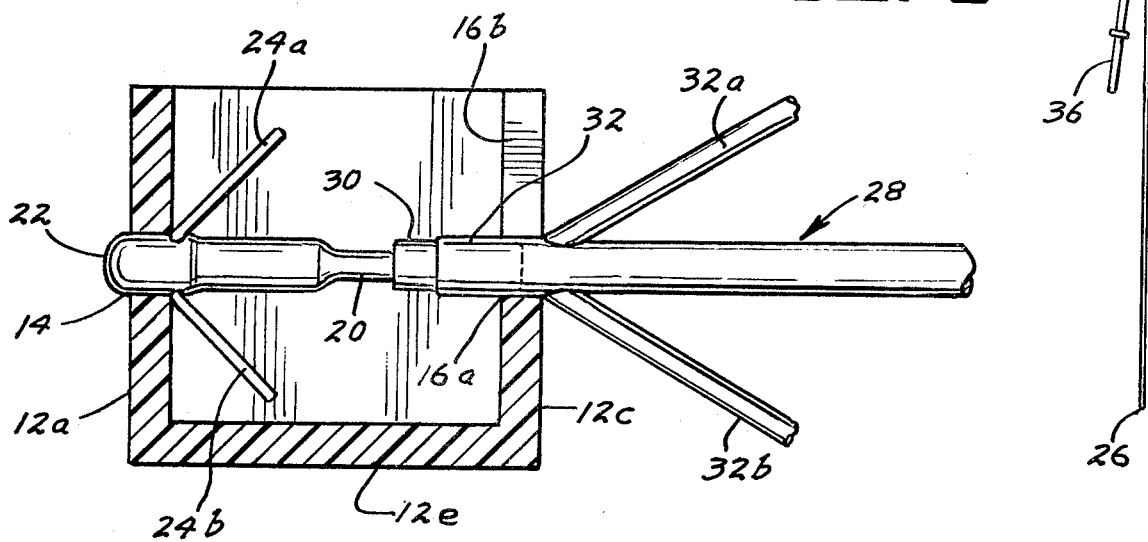
FIG. 3 is a cross-sectional view of the tine protector of FIG. 1 taken along line 3—3 of FIG. 1.

FIG. 1, which illustrates a top plan view of a tine protector 10, the present invention, shows a tine protector 10 including four sides 12a–12d in a square configuration and including a bottom 12e illustrated in FIG. 3. A first round hole 14 is positioned in substantially the center of the side 12a as illustrated in FIGS. 2 and 3. A second round hole 16a is geometrically aligned on the opposing side 12c with the hole 12a as illustrated in FIG. 3 and a longitudinal vertical slit 16b extends upwardly from the hole 16a to the top of the side 12c.

FIGS. 2 and 3 illustrate a perspective view and a cross section view respectively where all numerals correspond to those elements previously delineated.

PREFERRED MODE OF OPERATION

Transvenous lead 18 including a space-wound coil 20 covered with insulation, an electrode 22 of any known geometrical configuration axially secured over one end of the space-wound coil, a plurality of outwardly extending angular spaced tines 24 from a tine support body and a proximal tip 26 affixed to the other end of the space-wound coil 20 has the electrode end 22 supported by the tine protector 10 of the present invention as now described.

The electrode 22 frictionally engages into and within the first round hole 14 which has a diameter slightly smaller than the outer diameter of the electrode 22. The pacing lead having the space-wound coil 20 covered with insulation then fits through the longitudinal vertical slit 16b into the hole 16a as illustrated in FIG. 3. The width of slit 16b is less than the diameter of the hole 16a.

The disclosed embodiment of FIGS. 1–3 illustrates a second transvenous lead 28 coaxially positioned over the transvenous lead 18 and slid through the longitudinal vertical slit 16b to frictionally and snuggly engage within the hole 16a for support. The coaxial transvenous lead 28 includes a ring electrode 30 axially secured to the space-wound coil covered with insulation of the lead 28, a tine support body 32 including a plurality of outward angularly extending tines 32a and 32b. A fixation loop 34 secures to the tines 32a and 32b, and a connector pin 36 connects to the other end of the outer space-wound coil 28.

FIG. 2, which illustrates the perspective view of the tine protector 10, shows the transvenous leads 18 and 28 frictionally engaged in position in the walls 12a and 12c of the tine protector 10 as illustrated in the figures, especially FIG. 2. The plurality of tins 24a and 24b are securely protected within the confines of the tine protector 10 and the outwardly extending tines 32a and 32b which support and engage with the fixation loop 34 are protected by the outer confine of the wall 12c.

FIG. 3, which shows the cross-sectional view of the tine protector 10, shows the tines 32 and the fixation loop 34 protected and supported above the surface such as in a sterilized package housing the transvenous leads.

Figure 4:
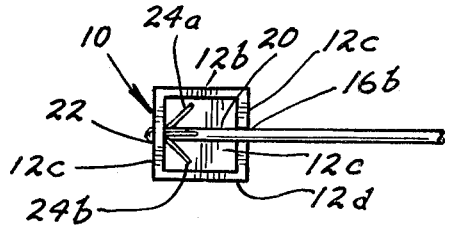
FIG. 4 is a plan view of a second embodiment of a tine protector supporting a pacing lead.

Various modifications can be made to the tine protector of the present invention without departing from the apparent scope thereof. Particularly, the tine protector 10 can support either the transvenous lead 18 within the confines of the tine protector 10 thereby providing spatial protection for the tines 24 as illustrated in FIG. 4, or in the alternative the tine protector could provide spatial protection solely for the transvenous lead 28 by providing spatial support for the fixation loop 34. In one of the many preferred embodiments, the tine protector 10 of the present invention has been disclosed supporting a coaxial transvenous lead, thereby protecting the tines 24 of the transvenous lead 18 and fixation loop 34 of the coaxial transvenous lead 28. While tines have been disclosed, any outwardly extending fixation structure for fixing the electrode in contact with the endothelial tissue composed of a material and configuration susceptible to creep and deformation can be utilized on the electrodes.

Having thus described the invention, there is claimed as new and desired to be secured by Letters Patent:

1. In combination, tine protector and transvenous pacing lead comprising:
   a. tine protector including four opposing walls and a bottom wall, said walls structurally connected together, a first round hole in one of said walls, and a longitudinal vertical slit and a second round hole in the other of said opposing wall, said round holes geometrically opposing each other;
   b. transvenous pacing lead including an electrode axially secured to a space-wound coil covered with insulation and a plurality of outward angularly extending tines from said electrode, and;
   c. said electrode frictionally engaged within and to said first hole and said space-wound coil covered with insulation of said lead frictionally engages within and to said second hole through said longitudinal vertical slit whereby said tines of said electrode lead are protected within the confines of said walls of said tine protector.

2. In combination, tine protector and coaxial transvenous leads including a fixation loop comprising:
   a. tine protector including four structurally connected walls and a bottom wall structurally connected to said four walls, a first round hole and a second round hole and slit in two of said opposing walls geometrically and substantially geometrically aligned with each other, and;
   b. coaxial transvenous leads including an inner transvenous lead having a wound coil covered with insulation, a electrode axially affixed to said coil and a plurality of tines extending outwardly from said electrode, said electrode supported in said first hole of said tine protector and an outer coaxial transvenous lead having an insulation covered space-wound coil, a ring electrode actually secured to said outer coil, two tines extending outwardly from said ring electrode, and a fixation loop secured to said tines, said ring electrode supported through said slit and in said second hole of said tine protector whereby said coaxial transvenous leads are supported within each of said respective opposing walls and said tines of said electrode are enclosed and protected within the confines of said tine protector and said tines of said outer coaxial transvenous leads and said fixation loop are protected by the confines of said outer opposing wall.

3. In combination, electrode protector and transvenous pacing lead comprising:
   a. tine protector including four opposing walls and a bottom wall, said walls structurally connected together, a first round hole in one of said walls, and a longitudinal vertical slit and a second round hole in the other of said opposing wall, said round holes geometrically opposing each other;
   b. transvenous pacing lead including an electrode axially secured to a space-wound coil covered with insulation and outwardly extending fixation menas for fixing said electrode in contact with endothelial tissue whereby said fixing means is susceptible to creep and deformation, and;
   c. said electrode frictionally engaged within and to said first hole and said space-wound coil covered with insulation of said lead frictionally engages within and to said second hole through said longitudinal vertical slit whereby said fixation means of said electrode lead are protected within the confines of said walls of said tine protector.

4. Apparatus comprising:
a body implantable lead having a proximal end, having a distal tip and having a tine extending angularly outward intermediate said proximal end and said distal tip;
a first support member having means for frictionally engaging said distal tip;
a second support member having means for frictionally engaging said body implantable lead intermediate said proximal end and said tine whereby said tine extends angularly outward from said body implantable lead between said first support member and said second support member; and
a plurality of additional support members coupled to said first support member and said second support member whereby said tine is protected.

* * * * *

UNITED STATES PATENT AND TRADEMARK OFFICE
CERTIFICATE OF CORRECTION

PATENT NO. : 4,262,678

DATED : April 21, 1981

INVENTOR(S) : Kenneth B. Stokes

It is certified that error appears in the above—identified patent and that said Letters Patent is hereby corrected as shown below:

Column 3, line 10, "tins" should read --tines--.

Column 4, line 7, "a" should read --an--.

Signed and Sealed this

Fifteenth Day of June 1982

[SEAL]

Attest:

GERALD J. MOSSINGHOFF

Attesting Officer        Commissioner of Patents and Trademarks